US00PP14778P3

(12) United States Plant Patent
Friday

(10) Patent No.: US PP14,778 P3
(45) Date of Patent: May 11, 2004

(54) P.F. 28-007 PEACH TREE ORIGIN OF VARIETY

(50) Latin Name: *Prunus persica*
Varietal Denomination: P.F. 28-007

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 9 days.

(21) Appl. No.: 10/087,960

(22) Filed: Mar. 5, 2002

(65) Prior Publication Data

US 2003/0172419 P1 Sep. 11, 2003

(51) Int. Cl.[7] ..... A01H 5/00
(52) U.S. Cl. ..... Plt./198
(58) Field of Search ..... Plt./198

*Primary Examiner*—Bruce R. Campell
*Assistant Examiner*—W C Haas

(57) ABSTRACT

A new and distinct variety of peach, *Prunus persica,* tree having the following unique combination of desirable features:

1. The new and distinct variety of peach tree is of average height and of upright growth and a regular and productive bearer of peaches.
2. Producing a very firm fruit having a resilient flesh texture.
3. Blossoms are non-showy when in full bloom.
4. A substantially oval spherical fruit with skin of dark red cover overlying a yellow which covers approximately twenty percent (20%) of its surface at maturity.
5. When harvested, the peduncle often remains affixed to the pit.
6. Late maturing fruit of good taste.
7. A late maturing fruit of good storage and shelf life.

2 Drawing Sheets

Botanical classification: *Prunus persica.*

ORIGIN OF VARIETY

The new peach tree (hereinafter referred to as the 'P.F. 28-007' peach tree) was originated by Paul Friday in the experimental orchard, which is maintained for the purposes of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. 28-007', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard of Paul Friday Farms Inc., located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of average height and of upright growth and a regular and productive bearer of peaches. A distinct characteristic of the 'P.F. 28-007' peach tree is its medium vigor having growth of about twenty-four inches (24") per year. The blossoms bloom in mid-season and are characterized by being contracted or partially spread to approximately ¾-inch when in full bloom. At the same time the five petals of the blossoms are of lesser length than the length of petals of the normal showy blossom as exemplified by the 'Loring' (unpatented) peach blossom.

The blossoms of the present peach tree at full bloom may be characterized as being non-showy. More specifically, the blossoms of the present peach tree have radially projecting and angularly spaced five blossom petals to form a blossom having a diameter of about ¾" measured across the blossoms.

The flesh of the fruit of the present peach tree is firm and is yellow. This variety is very freestone.

The skin is smooth having moderate to little down and is of dark red color overlying a yellow ground color. The yellow background covers approximately twenty percent (20%) of its surface at maturity. At maturity, the peach is spherical having an average diameter of about 2¾".

When harvested, the fruit is broken loose from the tree with the breaking point above the peduncle rather than below about fifty percent (50%) of the time.

The fruit produced by this tree has firm, and non-melting flesh, and thereby has the attendant resistance to blemishes and soft spots in harvesting, shipping and handling due to bruising. The firmness of the fruit flesh is sufficient to allow the flesh to yield and be restored when bumped or dropped without the resulting soft spots as would be experienced in most late season peaches of this market class. Thus, fruit of this tree remains more attractive to the ultimate buyer, the consumer, and thereby will command premium prices for the late fresh desert market.

The fruit matures in the latter part of the peach growing season of southwestern Michigan. The fruit as mentioned heretofore is of dark red color overlying a yellow, which covers approximately twenty percent (20%), of its surface and has a very attractive appearance.

BRIEF DESCRIPTION OF THE PHOTOGRAPHS

In the accompanying photographic illustrations, the top photograph shows three whole fruit depicting the substantially solid red blush of fruit skin coloration. The recessed pistil point of the fruit, the medium suture, and the exceptional shape and characteristic symmetry of the fruit of this tree are depicted in this photograph. A single peach as been bisected across the axis of the fruit to show the freestone characteristic and clear yellow flesh. A tape measure has been placed showing the extraordinary size that this new variety can obtain.

The bottom photograph shows the peduncle strongly affixed to the pit.

The next photograph shows the leaves of the plant, depicting both the upper and lower sides and length of the leaves.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System (PMS) as used internationally to identify printed colors.

Botanical classification: *Prunus persica* cultivar 'P.F. 28-007.'

Tree:
- *Age.*—Seven (7) years.
- *Height.*—Unpruned 14'.
- *Width.*—Unpruned 12'.
- *Size.*—Medium.
- *Vigor.*—Medium.
- *Density.*—Heavy — requires substantial pruning.
- *Form.*—Upright.
- *Production.*—Productive — requires a lot of thinning, even though it grows very large fruit.
- *Bearer.*—Consistent.
- *Disease resistance to bacterial leaf and fruit spot.*—Very good.

Trunk:
- *Bark.*—Gray (436).
- *Size.*—Medium.
- *Surface.*—Particularly smooth.
- *Diameter.*—4⅛"–24" above the ground at 7 years of age.

Branches:
- *Size.*—Medium — 2⅛" to 3" at trunk union.
- *Surface.*—Particularly smooth.
- *Lenticels per square inch on branch.*—Seven (7).
- *Lenticel color on branch.*—407.
- *Branch color.*—Grey (435).
- *Crotch angles.*—About 60 degrees average.

Leaves:
- *Size.*—Medium — average length 7" — average width 1 17/16".
- *Form.*—Lanceolate — pointed.
- *Thickness.*—Medium.
- *Texture.*—Glabrous.
- *Margin.*—Serrate.
- *Petiole.*—Length, 9/16" — medium thickness.
- *Gland.*—1 to 3 on each side of leaf base or upper portion of petiole.
- *Gland color.*—Brown red.
- *Gland shape.*—Oval.
- *Color.*—Upper surface green (554) — lower surface dull green (369).

Flower buds:
- *Size.*—½" long, 5/16" wide.
- *Shape.*—Ovoid.
- *Color.*—203.

Flowers:
- *Blooming period.*—May 3, 2001 to May 6, 2001.
- *Size of petals.*—½" long, 5/16" wide.
- *Shape of petals.*—Cupped.
- *Sepal size.*—¼" long, 3/16" wide.
- *Sepal shape.*—Cupped.
- *Sepal color.*—367.
- *Number of anthers.*—32.
- *Anther color.*—187.
- *Number of stamens.*—32.
- *Stamen color.*—464.
- *Pistil length.*—⅜".
- *Pistil color.*—393.
- *Pollen.*—Present, self-fertilizing.
- *Flower and petal color.*—230.
- *Petals per cluster.*—Five (5).
- *Flowers per cluster.*—Usually two (2).
- *Fragrance.*—Strong, not pleasant.

Fruit:
- *Maturity when described.*—Firm ripe.
- *Date of first picking.*—Sep. 12, 2001.
- *Date of last picking.*—Sep. 20, 2001.
- *Size.*—Very large — average diameter 2¾".
- *Form.*—Spherical.
- *Suture.*—Relatively smooth.
- *Weight.*—Average 9.6 oz.

Skin:
- *Thickness.*—Medium.
- *Texture.*—Medium.
- *Tendency to crack.*—None.
- *Down.*—Moderate.
- *Color.*—Medium red (214 to 207) mottled to yellow ground color (129).

Flesh:
- *Texture.*—Firm, non-melting.
- *Ripens.*—Relatively even.
- *Flavor.*—Excellent.
- *Aroma.*—Pleasant.
- *Eating quality.*—Very good.
- *Color.*—Clear yellow (120) — red around the pit and slight red into flesh (187).

Stone:
- *Type.*—Ovid.
- *Size.*—Average length 1½" — average width 1" — average thickness ¾".
- *Form.*—Ovid.
- *Base.*—Straight — peduncle often attached after harvest.

*Apex.*—Pointed.
*Sides.*—Nearly equal.
*Surface.*—Furrowed.
*Color.*—Reddish brown.
*Tendency to crack.*—Slight — about 2%.
*Kernel.*—5/8" long, 5/16" wide, 1/16" thick.
Use: Desert.
Shipping quality: Very good.
Keeping quality: Very good.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree, as herein illustrated and described.

1. Medium size, medium vigor and upright in growth—a regular and productive bearer of very large size yellow flesh freestone fruit with good flavor and shipping quality and having a late season maturity date of about Sep. 12, 2001.

* * * * *

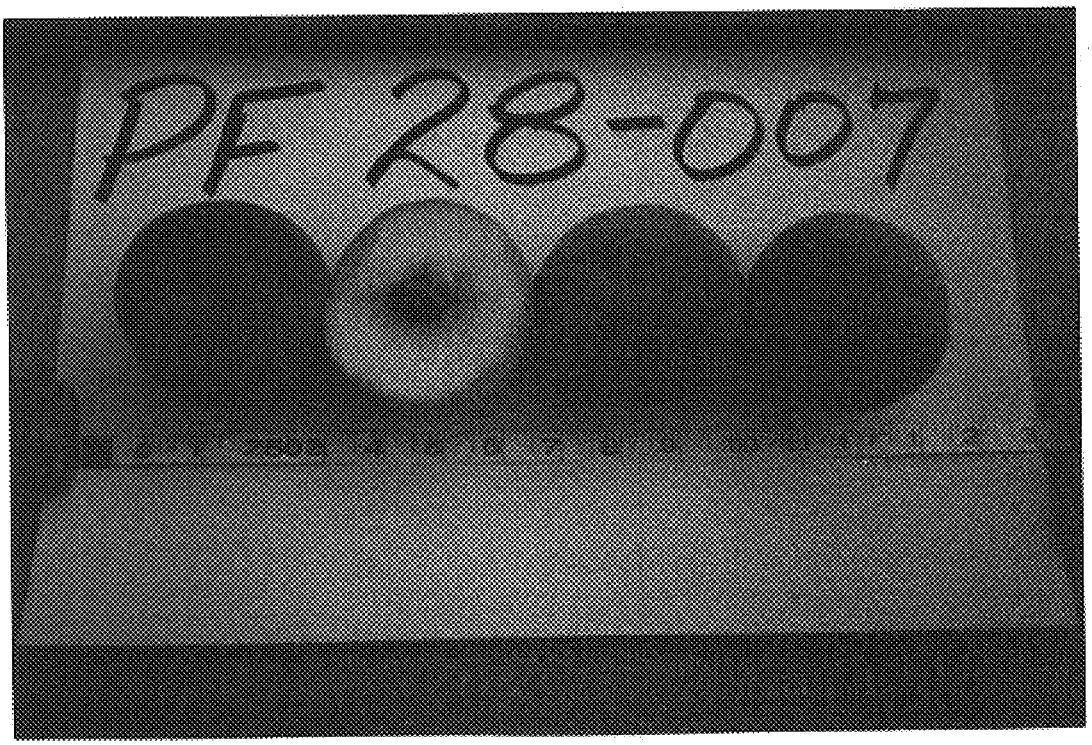
PF 28-007
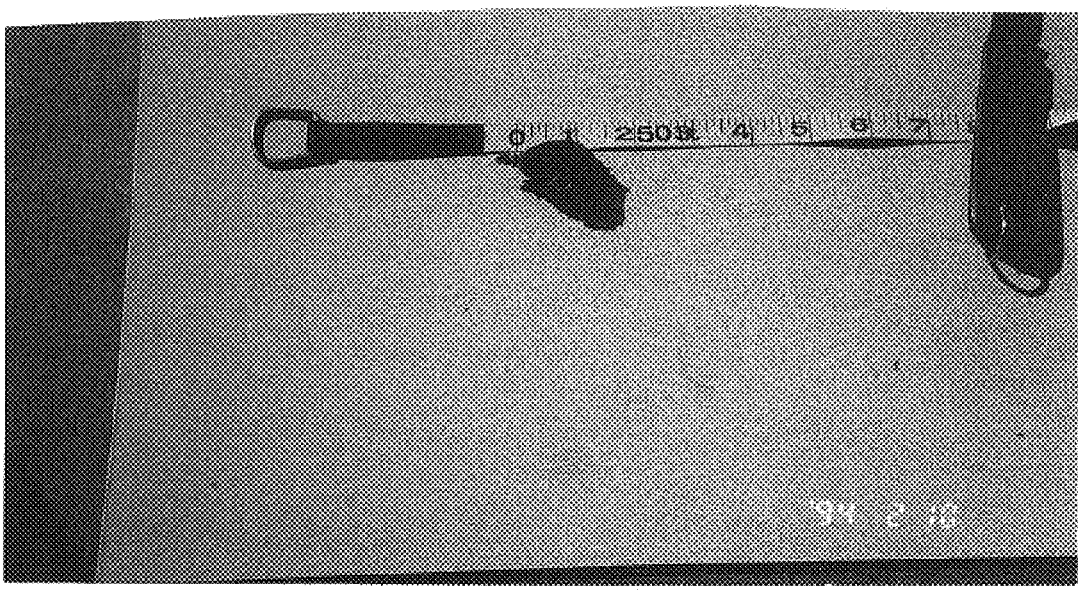

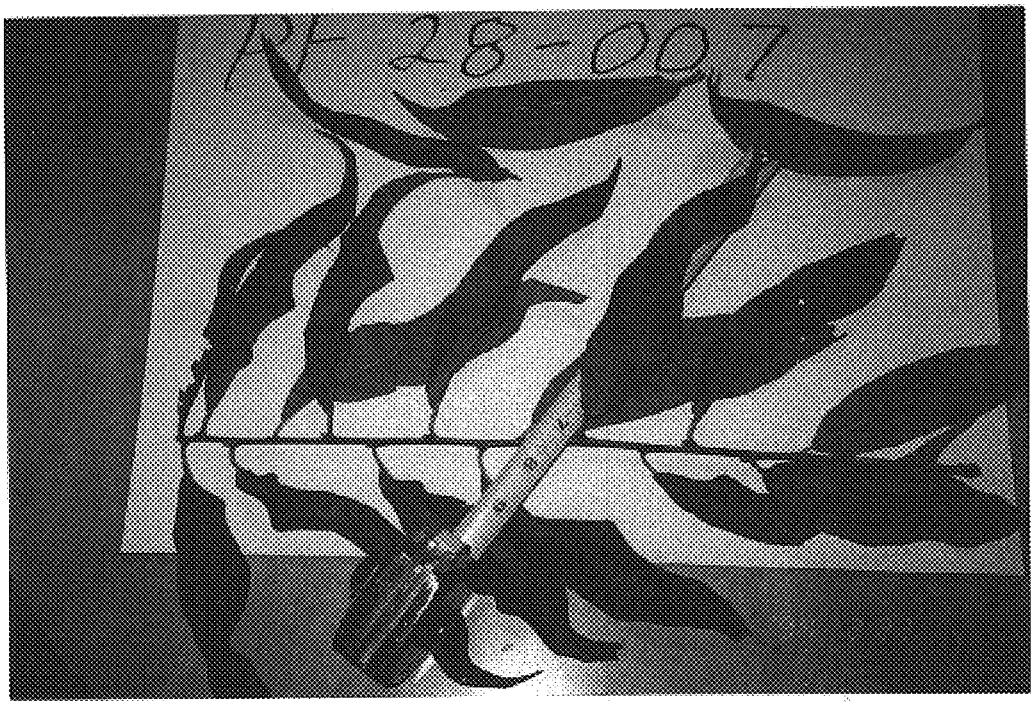
RF 28-007